US00PP36501P2

(12) United States Plant Patent
Suphachadiwong

(10) Patent No.: US PP36,501 P2
(45) Date of Patent: Feb. 25, 2025

(54) ***VANDA* PLANT NAMED 'SPCDW2303'**

(50) Latin Name: ***Vanda* sp. Jones ex R. Br.**
Varietal Denomination: SPCDW2303

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 18/831,220

(22) Filed: Sep. 25, 2024

(30) Foreign Application Priority Data

Sep. 28, 2023 (QZ) ..... PBR 20232030

(51) Int. Cl.
*A01H 6/62* (2018.01)
*A01H 5/02* (2018.01)

(52) U.S. Cl.
USPC ..... Plt./311

(58) Field of Classification Search
USPC ..... Plt./263.1, 311
See application file for complete search history.

(56) References Cited

U.S. PATENT DOCUMENTS

PP31,857 P3 * 6/2020 Suphachadiwong .... A01H 6/62
Plt./311

* cited by examiner

*Primary Examiner* — Karen M Redden
(74) *Attorney, Agent, or Firm* — Samuel R. McCoy, Jr.

(57) ABSTRACT

'SPCDW2303' is a new and distinctive *Vanda* plant which is characterized by improved plant vigor, large inflorescences with nearly all flowers open at the same time, relatively large and durable flowers, nearly pure white flowers, and stability of these characteristics from generation to generation.

3 Drawing Sheets

Latin name of the genus and species: The Latin name of the genus and species of the novel variety disclosed herein is *Vanda* sp. Jones ex R. Br.

Variety denomination: The inventive variety of *Vanda* disclosed herein has been given the variety denomination 'SPCDW2303'.

CROSS REFERENCE TO RELATED APPLICATIONS

This application claims priority to the Community Plant Variety Rights application number 2023/2030, filed Sep. 28, 2024, which is herein incorporated by reference.

BACKGROUND OF THE INVENTION

Parentage: The new *Vanda* plant, 'SPCDW2303', originated as a naturally-occurring whole plant mutation of *Vanda* 'SPCDW1405' (U.S. Plant Pat. No. 28,351). In November of 2015, the inventor discovered the whole-plant mutation at a commercial greenhouse in Bangphra, Thailand growing amongst a cultivated population of *Vanda* 'SPCDW1405'. The mutation was noted for its solid white flowers and was subsequently isolated for further evaluation in order to confirm the distinctness and stability of the characteristics first observed. Upon confirmation of distinctness and stability, 'SPCDW2303' was selected for commercialization.

Asexual Reproduction: Asexual reproduction of the new cultivar 'SPCDW2303', by way of mericloning, was first initiated in December of 2015 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through five subsequent generations, the unique features of this cultivar have proven to be stable and true to type.

SUMMARY OF THE INVENTION

The cultivar 'SPCDW2303' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW2303'. These characteristics in combination distinguish 'SPCDW2303' as a new and distinct *Vanda* cultivar:

1. *Vanda* 'SPCDW2303' exhibits an upright monopodial growth habit with large inflorescence borne above the foliage; and
2. *Vanda* 'SPCDW2303' exhibits improved plant vigor; and
3. *Vanda* 'SPCDW2303' exhibits inflorescences bearing flowers that all reach anthesis in short succession, yielding inflorescences with more open flowers; and
4. *Vanda* 'SPCDW2303' exhibits relatively large and durable flowers; and
5. *Vanda* SPCDW2303; exhibits flowers with petals, sepals, and a labellum that are nearly pure white at anthesis.

BOTANICAL DESCRIPTION OF THE PLANT

Figure 1:
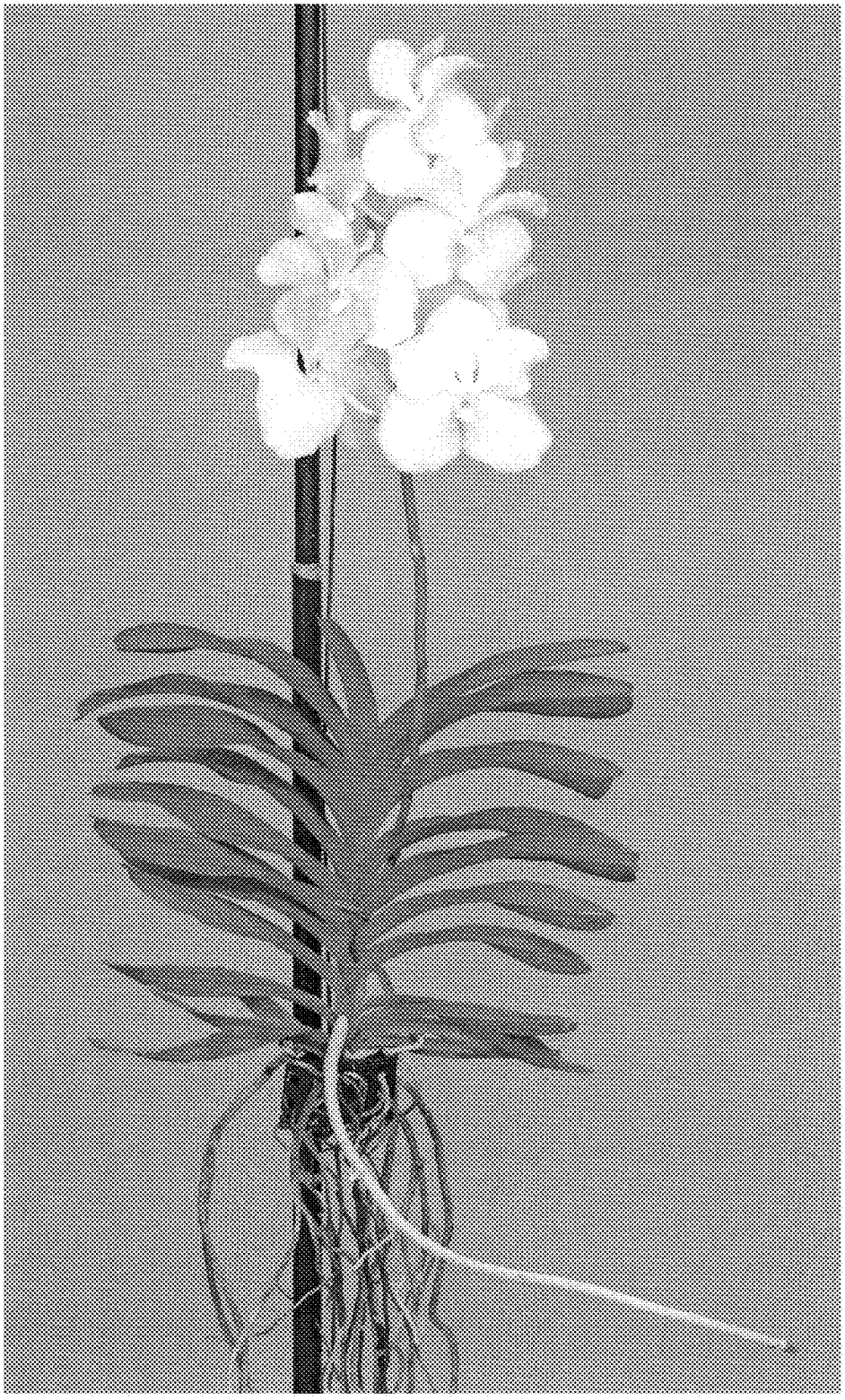
FIG. 1 illustrates, as nearly true as it is reasonably possible to make the same in color photographs of this type, an exemplary plant of 'SPCDW2303' grown in a commercial greenhouse in Honselersdijk, the Netherlands. This plant is approximately five years old from the time of mericloning, shown planted in an 8 by 8 cm container.
Figure 2:
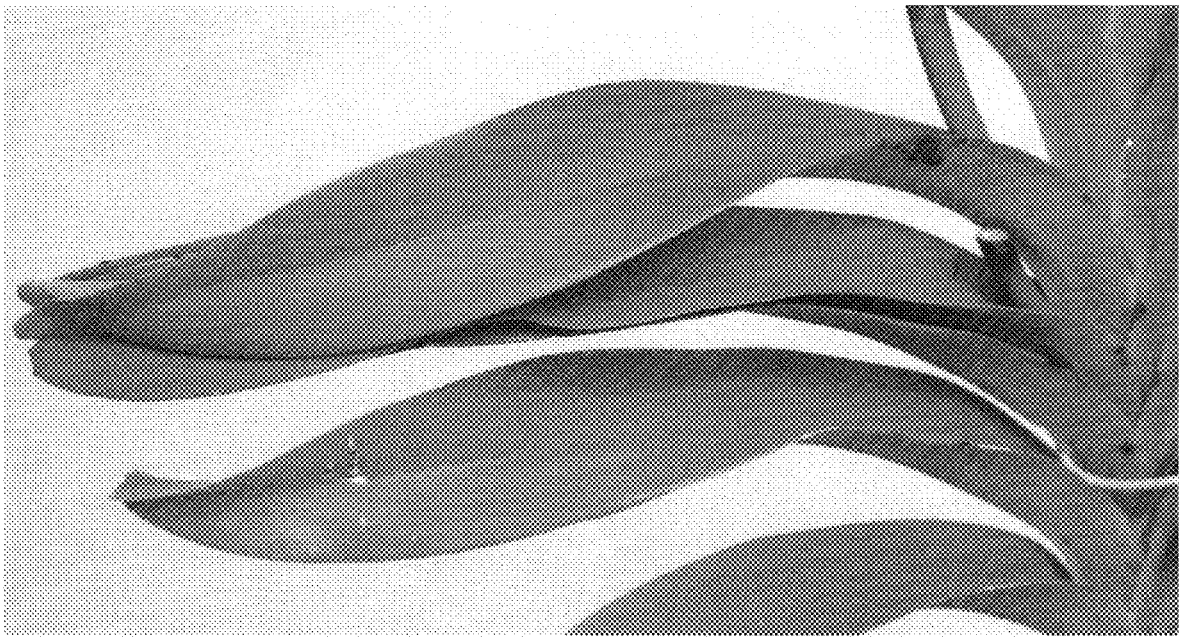
FIG. 2 illustrates, as nearly true as it is reasonably possible to make the same in color photographs of this type, the typical foliage of 'SPCDW2303'.
Figure 3:
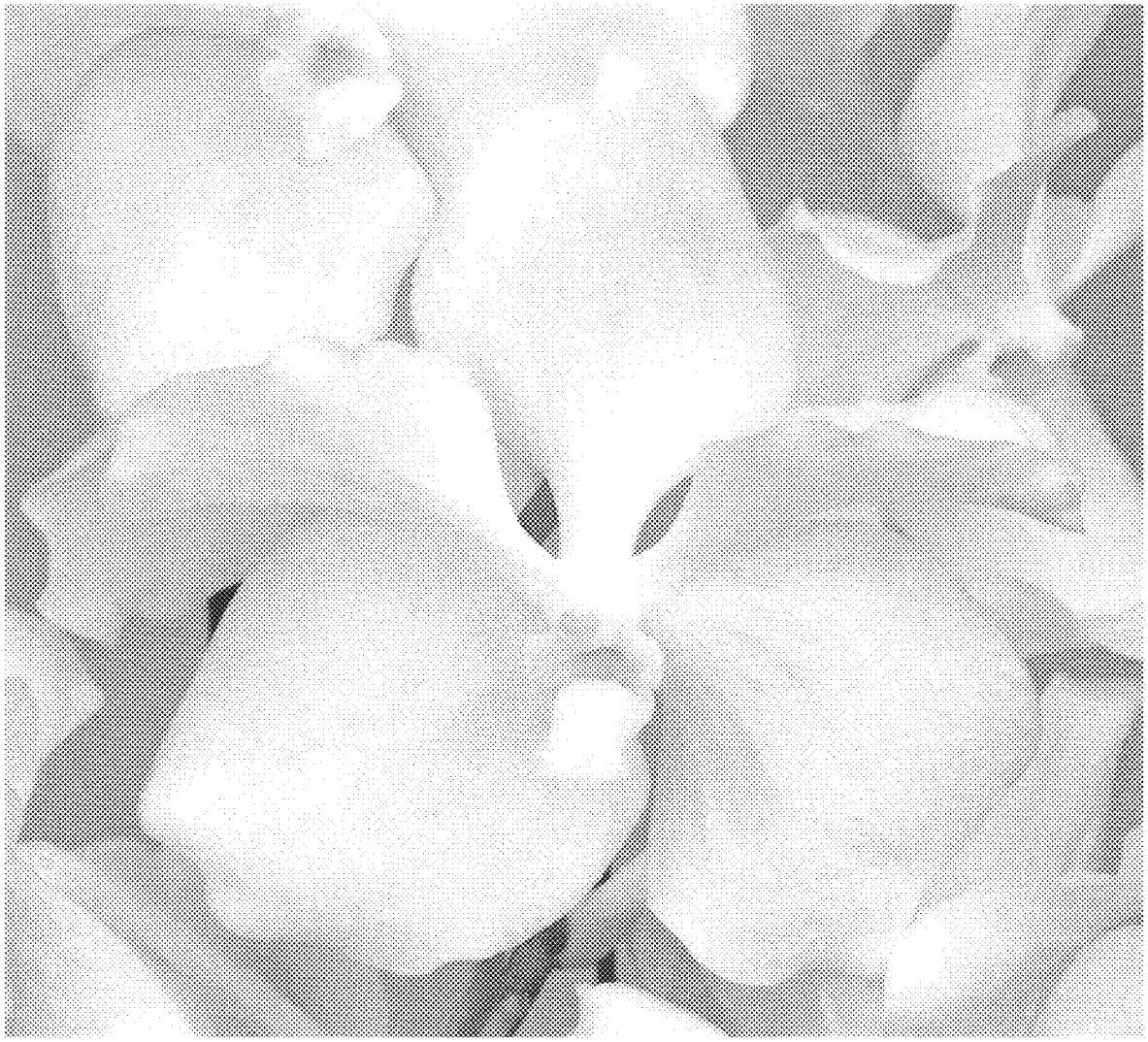
FIG. 3 illustrates, as nearly true as it is reasonably possible to make the same in color photographs of this type, the typical flower of 'SPCDW2303'.

The following observations and measurements made in July of 2024 describe averages from a sample set of six specimens of five-year-old 'SPCDW2303' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW2303' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, sixth edition.

A botanical description of 'SPCDW2303' and comparisons with the parent and most similar commercial variety of *Vanda* are provided below.

Plant description:

- *Growth habit*.—Perennial; monopodial, upright. Single monopodial leafy stem, with flowers carried above the leaf plane; inflorescences growing from the leaf axils.
- *Average height from base (plant grown in hanging basket, so no soil line present) to foliar plane*.—30.5 cm.
- *Average height from base (plant grown in hanging basket, so no soil line present) to top of floral plane*.—70.2 cm.
- *Plant spread*.—Average of 37.0 cm.
- *Growth rate*.—Moderate.
- *Plant vigor*.—Vigorous.
- *Propagation type*.—Meristematic tissue culture propagation using the base of the leaves.
- *Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility*.—Plants have not been observed to be susceptible or resistant to pathogens and pests common to *Vanda*.
- *Environmental tolerances*.—Adapt to, at least, USDA Zones 11 and 12 and temperatures as high as 40 degrees Celsius; high tolerance to rain; moderate to high tolerance to wind.

Root system:

- *General*.—Moderately to densely rooting; with aerial roots only.
- *Dimensions, mature roots*.—59.0 cm long with a diameter of 0.7 cm, on average.
- *Texture*.—Very fleshy; non-fibrous.
- *Color*.—Greyed-green, nearest to RHS 192C; root apex is yellow-green, RHS 144A.

Stem:

- *Branching habit*.—Monopodial; no lateral branches present.
- *Number of primary (main) stems per plant*.—One.
- *Number of secondary (lateral) branches per plant*.—None.
- *Aspect*.—Circular, formed by the leaf sheaths.
- *Length*.—22.0 cm.
- *Diameter*.—0.8 cm.
- *Internode length*.—0.8 cm.
- *Pubescence, texture and luster of stem*.—Glabrous and matte.
- *Attitude, main stem*.—Nearly vertical; average angle to vertical is 0-degrees.
- *Strength*.—Very strong.
- *Color, juvenile*.—Yellow-green, nearest to RHS 150D.
- *Color, mature*.—Green-white, nearest to RHS 157C.
- *Color at internodes*.—Green-white, nearest to RHS 157C.

Foliage:

- *Arrangement*.—Distichous.
- *Dimensions*.—19.8 cm long, excluding the sheath, and 3.0 cm wide.
- *Shape of blade*.—Ligulate; moderately to strongly carinate.
- *Aspect*.—A slight to moderate axial twist (i.e. spiraled).
- *Attitude*.—Slightly curled downward.
- *Apex*.—Unequal praemorse.
- *Base*.—Sheathing.
- *Sheath dimensions*.—3.1 cm long and 1.5 cm wide, on average.
- *Sheath color*.—Yellow-green to greyed-green nearest to RHS 144D and 193A.
- *Margin*.—Entire; no undulation.
- *Pubescence, texture and luster of adaxial surface*.—Glabrous and matte.
- *Pubescence, texture and luster of abaxial surface*.—Glabrous and matte.
- *Color*.—Juvenile foliage, adaxial surface — Green, nearest to RHS NN137B; becoming a lighter shade of green towards the midrib, nearest to RHS 137B. Juvenile foliage, abaxial surface — Yellow-green, nearest to RHS 146B; becoming darker towards the margins and apex, nearest to 137B. Mature foliage, adaxial surface — Green, nearest to RHS 143A. Mature foliage, abaxial surface — Yellow-green, nearest to in between RHS 146A; becoming green towards the margins and apex, nearest to RHS 143A.
- *Venation*.—Pattern — Parallel. Color, adaxial surface — Yellow-green, nearest to 146A. Color, abaxial surface — Yellow-green, nearest to 144A.
- *Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 10.

*Flowers per plant*.—9 open flowers and 1 flower bud.

*Inflorescence height*.—Approximately 28.5 cm (measured from base of lowest flower to top of upper flower).

*Inflorescence diameter*.—Approximately 21.2 cm.

*Peduncle*.—Dimensions — 48.0 cm long and 0.7 cm wide, on average. Attitude — 30-degree angle to lateral branch axis, on average. Strength — Moderately strong. Texture and luster — Glabrous and matte. Color — Green to yellow-green, nearest to a mixture of RHS 143C and 144C.

Bud:

*Length*.—2.2 cm, on average.

*Diameter*.—The horizontal diameter of 2.4 cm; the vertical diameter is 2.4 cm.

*Shape*.—Broad obovate to near globular, with a deltoid apex which is pointed downward.

*Pubescence, texture and luster*.—Glabrous, smooth, and slightly glossy.

*Color*.—White, nearest to RHS NN155A, fading to yellow-green towards the apex, nearest to RHS 150D.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the lateral petals are axially twisted slightly towards an outwardly facing horizontal orientation and strongly overlap the lateral sepals and dorsal sepal.

*Aspect*.—Flowers are outward-facing to slightly nodding.

*Vertical height*.—11.2 cm, on average.

*Diameter*.—11.1 cm, on average.

*Depth*.—4.5 cm, on average.

*Fragrance*.—No fragrance.

*Lastingness*.—3 weeks, on average.

*Persistent*.—Self-cleaning.

*Petals*.—Quantity of Petals — Three unfused petals. Arrangement — Two conventional lateral petals and one labellum, on average. Length — 5.5 cm, on average. Width — 4.7 cm, on average. Shape — Broad ovate. Apex — Obtuse. Base — Cuneate. Margin — Entire; moderately to highly undulated. Pubescence, texture and luster of adaxial side — Glabrous, velvety, and matte. Pubescence, texture and luster of abaxial side — Glabrous, velvety, and matte. Color, adaxial side — White, nearest to RHS NN155D. Color, abaxial side — White, nearest to RHS NN155D. Color when fully opened, adaxial side — White, nearest to RHS NN155D. Color when fully opened, abaxial side — White, nearest to RHS NN155D. Fading, adaxial side — Not fading. Fading, abaxial side — Not fading. Venation color, fully opened, adaxial side — White, nearest to RHS NN155D. Venation color, fully opened, abaxial side — White, nearest to RHS NN155D.

*Labellum*.—Shape — Three-lobed; the lateral lobes are obovate and involute; the central lobe is broad oblong and moderately revolute. Length — Central lobe — Approximately 2.2 cm. Lateral lobes — Approximately 1.0 cm. Width — Central lobe — Approximately 1.2 cm at the base; 1.2 at the apex. Lateral lobes — Approximately 0.6 cm. Apex — Central lobe — Emarginate. Lateral lobes — Unequal emarginate. Base — Central lobe — Cuneate. Lateral lobes — Cuneate. Margin — Central lobe — Entire; moderately undulated. Lateral lobes — Entire; not undulated. Texture and luster of adaxial side — Central lobe — Glabrous, velvety, and matte. Lateral lobes — Glabrous, velvety, and matte. Texture and luster of abaxial side — Central lobe — Glabrous, velvety, and matte. Lateral lobes — Glabrous, velvety, and matte. Color when opening, adaxial side — Central lobe — White, nearest to RHS NN155B. Lateral lobes — White, nearest to RHS NN155A; base is yellow, nearest to RHS 13A and 13B. Color when opening, abaxial side — Central lobe — White, nearest to RHS NN155B. Lateral lobes — White, nearest to RHS NN155C; base is greyed-white, nearest to 156D. Color when fully opened, adaxial side — Central lobe — White, nearest to RHS NN155C. Lateral lobes — White, nearest to RHS NN155C; base is yellow, nearest to a mixture of RHS 12A and 12B. Color when fully opened, abaxial side — Central lobe — White, nearest to RHS NN155C. Lateral lobes — White, nearest to RHS NN155C; base is yellow, nearest to RHS 11D. Fading, adaxial side — Not fading. Fading, abaxial side — Not fading. Venation — No visible venation. Venation color, fully opened, adaxial side — Central lobe — No visible venation. Lateral lobes — No visible venation. Venation color, fully opened, abaxial side — Central lobe — No visible venation. Lateral lobes — No visible venation.

*Callosities*.—Dimensions — 1.7 cm long and 0.7 cm wide, on average. Color — White, nearest to RHS NN155C.

*Spurs*.—Quantity — Average of 1. Length — Approximately 1.0 cm. Diameter — Approximately 0.4 cm. Vertical height — Approximately 0.7 cm, at the base. Shape — Short triangular; flattened. Apex — Bluntly acute. Base — Broad cuneate. Pubescence, texture and luster — Glabrous, smooth, and matte. Color — White, nearest to RHS 155C; and radially striped nearest to NN155A.

*Sepals*.—Quantity — Average of 3 unfused sepals. Arrangement — One dorsal sepal and two lateral sepals. Length — Dorsal sepal — Approximately 5.9 cm. Lateral sepals — Approximately 6.4 cm. Width — Dorsal sepal — Approximately 4.9 cm. Lateral sepals — Approximately 5.9 cm. Shape — Dorsal sepal — Broad ovate. Lateral sepals — Broad ovate. Apex — Dorsal sepal — Shallow retuse. Lateral sepals — Obtuse. Base — Dorsal sepal — Cuneate. Lateral sepals — Cuneate. Margin — Dorsal sepal — Entire; coarsely moderately undulated. Lateral sepals — Entire; strongly to moderately undulated. Pubescence, texture and luster, adaxial side — Dorsal sepal — Glabrous, velvety, and matte. Lateral sepals — Glabrous, velvety, and matte.

Pubescence, texture and luster, abaxial side — Dorsal sepal — Glabrous, velvety, and matte. Lateral sepals — Glabrous, velvety, and matte. Color when opening, adaxial side — Dorsal sepal — White, nearest to RHS NN155D. Lateral sepals — White, nearest to RHS NN155D. Color when opening, abaxial side — Dorsal sepal — White, nearest to RHS NN155D. Lateral sepals — White, nearest to RHS NN155D. Color when fully opened, adaxial side — Dorsal sepal — White, nearest to RHS NN155D. Lateral sepals — White, nearest to RHS NN155D. Color when fully opened, abaxial side — Dorsal sepal — White, nearest to RHS NN155D. Lateral sepals — White, nearest to RHS NN155D. Fading, adaxial side — Not fading. Fading, abaxial side — Not fading. Venation color, fully opened, adaxial side — Dorsal sepal — White, nearest to RHS NN155D. Lateral sepals — White, nearest to RHS NN155D. Venation color, fully opened, abaxial side — Dorsal sepal — White, nearest to RHS NN155D. Lateral sepals — White, nearest to RHS NN155D.

*Pedicels*.—Length — 5.8 cm, on average. Diameter — 0.4 cm, on average. Attitude — 55-degree angle to peduncle axis, on average. Strength — Moderately strong. Texture — Glabrous. Aspect — Striated, with 5 angular ribs, due to resupination. Luster — Moderately glossy. Color — White, nearest to RHS NN155D, becoming slightly darker to a green-white towards the proximal end, nearest to RHS 157D.

*Bract*.—Quantity — One bract present at the base of each pedicel. Shape — Reniform; strongly concave, folded around the base of each pedicel. Dimensions — 1.7 cm long and 1.6 cm wide, on average. Apex — Broad obtuse. Base — Broad cuneate. Margins — Entire. Color, inner surface — Yellow-green, nearest to RHS N144D. Color, outer surface — Yellow-green, nearest to RHS N144D.

Reproductive organs:

*Column*.—Length — 0.6 cm, on average. Diameter — 0.7 cm, on average. Color — White, nearest to RHS NN155A.

*Stigma*.—Shape — Reinform. Length — 0.3 cm, on average. Diameter — 0.4 cm, on average. Color — White, nearest to 155C.

*Ovary*.—Position — Inferior. Length — 0.8 cm, on average. Diameter — 0.15 cm, on average. Color — Yellow-green, nearest to RHS 150C.

*Pollinia*.—Diameter — 0.3 cm, on average (per pair of pollinia). Color — Yellow-orange, nearest to RHS 14A.

Seed and fruit: No fruit and seed production has been detected to date.

COMPARISON WITH THE PARENT PLANT

Plants of the new cultivar 'SPCDW2303' differ from the parent, *Vanda* 'SPCDW1405' (U.S. Plant Pat. No. 28,351), by the characteristics described in Table 1.

TABLE 1

| Characteristic | 'SPCDW2303' | 'SPCDW1405' |
|---|---|---|
| Plant vigor. | More vigorous than 'SPCDW1405'. | Less vigorous than 'SPCDW2303'. |
| General coloration of the petals and sepals when fully opened. | Near pure white. | Very light violet to white coloration. |
| Sepal and petal tessellation. | None exhibited. | Pronounced light blue tessellation. |
| Flower durability. | More durable than 'SPCDW1812'. | Less durable than 'SPCDW2303'. |

COMPARISON WITH THE MOST SIMILAR *VANDA* CULTIVAR KNOWN TO THE INVENTOR

Plants of the new cultivar 'SPCDW2303' are similar to the cultivar, *Vanda* 'SPCDW1812' (U.S. Plant Pat. No. 31,857). A comparison of 'SPCDW2303' with *Vanda* 'SPCDW1812' is described in Table 2.

TABLE 2

| Characteristic | 'SPCDW2303' | 'SPCDW1812' |
|---|---|---|
| Plant vigor. | More vigorous than 'SPCDW1812'. | Less vigorous than 'SPCDW2303'. |
| Root system. | More densely rooted, with longer and thicker roots that are more durable than those of 'SPCDW1812'. | Less densely rooted, with shorter and thinner roots that are more fragile than those of 'SPCDW2303'. |
| Inflorescence. | Larger than 'SPCDW1812', with more open flowers. | Smaller than 'SPCDW2303' with fewer open flowers. |
| Flower size. | Larger than 'SPCDW1812'. | Smaller than 'SPCDW2303'. |
| General coloration of the flower. | Nearer to pure white relative to 'SPCDW1812'. | White, occasionally with light yellow suffusion as petals age. |
| Petal size. | Larger than 'SPCDW1812'. | Smaller than 'SPCDW2303'. |
| Lateral and dorsal sepal sizes. | Smaller than 'SPCDW1812'. | Larger than 'SPCDW2303'. |
| Lateral sepal shape. | Broad ovate. | Reniform. |
| Lateral sepal color. | White with yellow blotches at the base. | White with yellow-orange blotches at the base. |
| Dorsal sepal shape. | Broad ovate. | Near orbicular. |
| Flower durability. | More durable than 'SPCDW1812'. | Less durable than 'SPCDW2303'. |

That which is claimed is:

1. A new and distinct variety of *Vanda* plant named 'SPCDW2303', substantially as described and illustrated herein.

* * * * *